United States Patent [19]

Stampfer

[11] Patent Number: 4,808,532

[45] Date of Patent: Feb. 28, 1989

[54] CONTINUOUS HUMAN CELL LINES AND METHOD OF MAKING SAME

[75] Inventor: Martha R. Stampfer, Oakland, Calif.

[73] Assignee: The United States of America as represented by the United States Department of Energy, Washington, D.C.

[21] Appl. No.: 750,124

[22] Filed: Jul. 1, 1985

[51] Int. Cl.⁴ .......................... C12N 5/00; C12Q 1/68; C12Q 1/02; C12Q 1/18

[52] U.S. Cl. .................................... 435/240.2; 435/6; 435/29; 435/32; 435/948; 935/71

[58] Field of Search ........................ 435/6, 29, 32, 240, 435/172.3, 71, 240.2

[56] References Cited

U.S. PATENT DOCUMENTS

| | | | |
|---|---|---|---|
| 3,871,954 | 3/1975 | Zuckerman | 195/1.1 |
| 3,935,066 | 1/1976 | Apostolov | 195/1.7 |
| 4,393,133 | 7/1983 | Knowles et al. | 435/6 |
| 4,423,145 | 12/1983 | Stampfer et al. | 435/32 |
| 4,434,230 | 2/1984 | Ritts, Jr. | 435/240 |
| 4,465,769 | 8/1984 | Hampar et al. | 435/6 |
| 4,469,790 | 9/1984 | Yamane et al. | 435/68 |
| 4,472,500 | 9/1984 | Milstein et al. | 435/68 |
| 4,477,567 | 10/1984 | Healy et al. | 435/71 |
| 4,491,632 | 1/1985 | Wands et al. | 435/240 |

OTHER PUBLICATIONS

MacNicoll, et al., Biochemical and Biophysical Research Communications 95(4), pp. 1599–1606 (1980).

Yang et al., Cancer Research 41, pp. 1021–1027 (1981).

Bartley et al., *Metabolism of Benzo[a]pyrene by Human Epithelial and Fibroblastic Cells...*, J. Cell Biochem. 18: 135–148 (1982).

Emerman, et al., *Glucose Metabolite Patterns as Markers of Functional Differentiation...*, Exp. Cell Res. 134: 241–250 (1981).

Greiner, et al., *Carcinogen–Induced Phenotypic Alterations in Mammary Epithelial Cells*, Cancer Res. 43: 273–278 (1983).

Hackett, et al., *Two Syngeneic Cell Lines from Human Breast Tissue...*, J. Nat'l Cancer Inst. 58(6): 1795–1806 (1977).

Halton, et al., *Cell Culture Quality Control by Rapid Isoenzymatic Characterization*, in Vitro 19(1): 16–24 (1983).

Milo, et al., *Neoplastic Transformation of Human Epithelial Cells in Vitro After Exposure to Chemical Carcinogens*, Cancer Res. 41: 5096–5102 (1981).

Smith, et al., *Thioesterase II, a New Marker Enzyme for Human Cells of Breast Epithelial Origin*, JNCI 73(2): 323–329 (1984).

Stampfer, et al., *Fibronectin Production by Human Mammary Cells*, JNCI 67(2): 253–261 (1981).

Stampfer, *Growth of Human Mammary Epithelial Cells in Culture* in "Methods for Serum–Free Culture of Cells of the Endocrine System" pp. 171–182 (1984).

Stampfer, et al., *Growth of Normal Human Mammary Cells in Culture*, in Vitro 16(5): 415–425 (1980).

Stampfer, et al., *Induction of Transformation and Continuous Cell Lines from Normal Human Mammary Epithelial Cells...*, Proc. Natl. Acad. Sci. USA 82 (1985).

Stampfer, et al., *Metabolism of Benzo[a]pyrene by Human Mammary Epithelial Cells...*, Proc. Natl. Acad. Sci. USA 78(10): 6251–6255 (1981).

DiPaolo, "Relative Difficulties in Transforming Human and Animal Cells in Vitro", JNCI, 70:1, Jan. 1983, pp. 3–8.

Harris, "Human Tissues and Cells in Carcinogenesis Research", Cancer Research, 47:1–10, Jan. 1, 1987, pp. 1–10.

*Primary Examiner*—John Edward Tarcza
*Attorney, Agent, or Firm*—L. E. Carnahan; Roger S. Gaither; Judson R. Hightower

[57] ABSTRACT

Substantially genetically stable continuous human cell lines derived from normal human mammary epithelial cells (HMEC) and processes for making and using the same. In a preferred embodiment, the cell lines are derived by treating normal human mammary epithelial tissue with a chemical carcinogen such as benzo[a]pyrene. The novel cell lines serve as useful substrates for elucidating the potential effects of a number of toxins, carcinogens and mutagens as well as of the addition of exogenous genetic material. The autogenic parent cells from which the cell lines are derived serve as convenient control samples for testing. The cell lines are not neoplastically transformed, although they have acquired several properties which distinguish them from their normal progenitors.

4 Claims, No Drawings

CONTINUOUS HUMAN CELL LINES AND METHOD OF MAKING SAME

The Government has rights in this invention pursuant to Contract No. DE-APO3-84SF15389 awarded by the United States Department of Energy.

FIELD OF THE INVENTION

This invention relates generally to human cell lines useful for testing potential mutagenic or carcinogenic agents, and in particular relates to continuous cell lines developed from human mammary epithelial cells.

BACKGROUND OF THE INVENTION

Studies of normal and pathological human cell physiology require appropriate cell culture systems, since in vivo experiments are not possible. The mammary gland provides an excellent source of human cells for culture, since abundant amounts of tissue are available from several commonly performed surgical procedures such as reduction mammoplasties, biopsies, gynecomastias, and mastectomies. In particular, mammary gland epithelial cells in culture can serve as valuable substrates for studies on carcinogenesis, differentiation, and basic cellular and molecular mechanisms. In vivo, the breast glandular epithelial cells are the cell type responsible for expression of the differentiated functions associated with synthesis of milk products; this behavior is under specific hormonal control. The breast epithelial cells are also the source of the second most common cancer in this country.

Eighty-five to ninety per cent of human cancers originate in epithelial cells. However, while transformation of cultured human fibroblastic and stromal cells by chemical carcinogens and radiation has been done, transformation in vitro of human epithelial cells has proved more difficult. Although epithelial cell cultures derived from numerous organs of rodent model systems have been neoplastically transformed by chemical carcinogens, little work has been done regarding carcinogen-induced transformation of human epithelial organ or cell cultures. Results obtained with rodents are not necessarily applicable to humans, and it is thus preferable to conduct experimentation with human cells directly. At present, however, there are no known continuous cell lines that have been verified as human mammary epithelium in origin are not virus transformed and which are useful for studying the effects of toxins, carcinogens and mutagens.

It is also preferable to conduct experimentation with continuous rather than with normal cell lines which have a finite life span, as work with the continuous cell lines is substantially more convenient. Furthermore, since carcinogenic events are most likely to occur during cell replication, and actively dividing cell culture system is strongly preferred. Previously, continuous cell lines were obtainable from two sources: from tumor cells, which can spontaneously transform to continuous at a low frequency, and in some cases, from normal cells which have been infected with a tumor virus or oncogenic material. These cell lines generally have an unstable chromosome complement, however, and thus are not particularly useful for studying carcinogenesis or mutagenesis.

There is thus a need in the art for a substantially genetically stable continuous human cell line useful in the study of the effects of chemicals and drugs considered to be potential toxins, carcinogens or mutagens. The present invention addresses this need and others by providing such a cell line derived from normal human mammary epithelial cells.

SUMMARY OF THE INVENTION

Accordingly, it is an object of the invention to provide a substantially genetically stable continuous human cell line useful for the study of compounds considered to be potential toxins, carcinogens or mutagens.

It is another object of the invention to provide an in vitro transformation assay with such a cell line using human mammary epithelial cells, which assay is useful for studying the effects of addition of exogenous genetic material.

It is still another object of the invention to provide a process for obtaining a substantially genetically stable continuous human cell line useful for the study of potentially toxic, carcinogenic, or mutagenic compounds.

It is yet another object of the invention to provide such a process in which the cell line is obtained by treatment of normal human mammary epithelial cells with a chemical carcinogen.

It is a further object of the invention to provide a method of testing the toxicity, carcinogenicity or mutagenicity of compounds using a substantially genetically stable continuous human cell line.

It is still another object of the invention to provide a method for testing the effects of adding exogenous genetic material to a continuous human cell line derived from normal human mammary epithelial tissue.

Further objects and advantages of this invention will become apparent from the study of the following portion of the specification and the appended claims.

In one aspect of the present invention, extended life (EL) cultures are prepared which are derived from normal human mammary epithelial cells by treating the cells with a chemical carcinogen such as benzo[a]pyrene. Using an appropriate medium, continuous cell lines emerge from these EL cultures which may subsequently be put to a number of uses, including testing for the effects of potential toxins, carcinogens or mutagens, screening monoclonal antibodies, and testing for the effects of addition of exogenous genetic material on these and equivalent cell lines.

DETAILED DESCRIPTION OF THE INVENTION

The present invention provides two novel continuous cell lines that are obtained by transformation of normal human mammary epithelial cells (HMEC) with a chemical carcinogen such as benzo[a]pyrene. The cell lines do not display properties associated with malignant transformation, although they have acquired several properties that distinguish them from their normal progenitors and which are more characterisic of tumor-derived human mammary epithelial cells. The continuous cell lines thus represent immortal rather than neoplastic transformants, and so are able to provide very convenient substrates for attempts to induce expression of further neoplastic properties by utilizing chemical carcinogens, potential promoters, and viral or cellular oncogenic material.

Two continuous cell lines in accordance with this invention have been designated 184A1 and 184B5 and are deposited with the American Type Culture Collection of Rockville, Md., under accession numbers ATCC CRL8798 and CRL8799. Although this indicated public availability is the simplest method of obtaining a cell line in accordance with this invention, it is not altogether unlikely that similar and functionally related cell lines may be produced by procedures other than those described herein. Such functionally and morphologically substantially identical cell lines, including derivatives of there cell lines, clones or subclones thereof, and future cell lines generated by related techniques, are to be considered equivalent to cell lines 184A1 and 184B5 and are therefore included within the scope of this invention.

The continuous cell lines are generally provided as a cell culture of the cell lines in a nutrient culture medium. One nutrient culture medium that can be used is that set forth in U.S. Patent No. 4,423,145 to Stampfer et al., the disclosure of which is hereby incorporated by reference in its entirety.

The cell lines can be provided using the following general method. Cells are first derived from normal human breast epithelial tissue in such a way that clumps of cells obtained are substantially free from attached stroma. The cells are then cultured in a medium which is effective to promote cell growth. Rapidly dividing cell cultures are then exposed to one or more doses of chemical carcinogen. Effective carcinogens include polycyclic aromatic hydrocarbons such as benzo[a]pyrene. While a wide range of doses may be effective to provide the novel cell lines, a preferred dose is approximately 80% inhibitory, i.e. about 80% of the cells exposed are killed. After exposure, "extended life" (EL) cultures are prepared by allowing time for numerous subsequent cell divisions. The cell lines of the present invention may then emerge from the EL cultures, by virtue of clonal events having occurred which give rise to these immortal cells.

The cell lines obtained, designated 184A1 and 184B5, can then be used to test the effect of various chemicals and drugs considered to be toxins, carcinogens or mutagens using the autogenic parent cells as a control. As the lines are "partially" transformed—that is, neither completely neoplastically transformed nor completely normal—they are especially useful for this purpose. Another potential use of the new cell lines may be to screen monoclonal antibodies. Finally, the cells can also be used to test for the effects of addition of exogenous genetic material. Thus, in a preferred embodiment, the invention includes the new cell lines 184A1 and 184B5, all functionally and morphologically equivalent cell lines, a process for creating the cell lines, and a process for using the cell lines.

METHODS

Media. Two different growth media were employed, one of which is disclosed in U.S. Pat. No. 4,423,145 to Stampfer, et al., incorporated by reference above. This latter medium (MM) consisted of a 1:1 mixture of Dulbecco's modified Eagle's medium and Ham's F-12 medium with the undefined elements of 0.5% fetal bovine serum and conditioned media from the human bladder epithelial cell line Hs767Bl and/or the human fetal intestine epithelial cell line Hs74Int (30%) (see Owens, et al., *J. Natl. Cancer Inst.* 56, 843–849 (1976)) and the human myoepithelial cell line Hs5780Bst (10%) (see Hackett, et al., *J. Natl. Cancer Inst.* 58, 1795–1806 (1977)) as well as insulin (10 µg/ml), hydrocortisone (0.1 µg/ml), epidermal growth factor (5 ng/ml), estrogen (1 nM), triiodothyronine (0.01 µM), and cholera toxin (1 ng/ml). A serum-free medium, MCDB170 (see, e.g., Hammond, et al., *Proc. Natl. Acad. Sci. USA* 78, 6251–6255), was also prepared, containing insulin (5 µg/ml), hydrocortisone (0.14 µM), epidermal growth factor (10 ng/ml), ethanolamine (0.1 mM), phosphoethanolamine (0.1 mM), transferring (5 µg/ml), and bovine pituitary extract (70 µg/ml). Where determined to be necessary, isoproterenol (1 µM) or cholera toxin (1 ng/ml) was also added to this latter medium.

Processing of Mammary Tissue. Reduction mammoplasty tissue from a 21-year-old woman with no detectable breast epithelial cell pathology was utilized (which will sometimes hereinafter be referred to as "specimen number 184"). The fresh surgically removed tissue was processed for separation of epithelial organoids from stromal components as follows.

The epithelial cells were separated from the stromal cells by a procedure involving dissection, enzymatic digestion, and filtration. In nontumor specimens, epithelial areas generally appear as white strands embedded in the stromal matrix of adipose tissue, connective tissue, and blood vessels. These areas were identified and gently dissected out by use of a combination of scalpel, forcep, and scissor to scrape away the grossly fatty material and lacerate the epithelialappearing areas. The minced epithelial-containing tissue was placed in a conical centrifuge tube with the tissue comprising no greater than a third of the volume of the tube. The tube was brought up to full volume, leaving only a small air space to allow for gentle mixing during rotation, using tissue digestion mixture (Ham's F-12, 10µg/ml insulin, antibiotics) and a final concentration of 10% fetal calf serum (FCS), 200 U/ml crude collagenase, and 100 U/ml hyaluronidase (Sigma Chemical Co., St. Louis, MO). The collagenase in the enzyme mixture served to break down the stroma, whereas the hyaluronidase digested the basement membrane, producing organoid structure containing epithelial and myoepithelial cells. The tubes were placed on a tube rotator and incubated overnight at 37° C. The next day, the tubes were centrifuged at 600g for 5 min., the pelleted material was resuspended in a fresh tissue digestion mixture, FCS, and enzymes, and the tubes were reincubated with rotation at 37° C. Most tissue samples required an additional round of centrifugation and resuspension overnight in fresh tissue digestion/enzyme mixture. The incubation was completed when microscopic examination showed clumps of cells (organoids) with ductal, alveolar, or ductularalveolar structures free from attached stroma.

When digestion was completed, the material was centrifuged and resuspended in a small volume of medium. It was then placed on a sterile polyester filter of 150-µm pore size (Pecap Monofilament polyester screen, Tetko, Inc., Monterey Park, CA), consisting of a 3"×3" piece of filter screen held rigid between two metal plates containing a 2" diameter center opening. After collection of a filtrate by gravity, the material remaining of the filter was collected by inverting the filter and washing the collected material into a 50-ml centrifuge tube. The material remaining in the filtrate was placed on a 95-µm filter (the size of the filters used selected to correspond to the size of the cell clumps obtained), and the collection process was repeated to harvest the smaller epithelial clumps. The material collected on the different-sized filters, and the filtrate, were each centrifuged and the pellets were resuspended in cell preservative medium (Dulbecco's modified Eagle's medium [DME], 15% FCS, 10% dimethylsulfoxide [DMSO]), with a 10:1 volume of medium to volume of the packed cell pellet. Aliquots containing about 0.1 ml each of pelleted cells were slowly frozen to −70° C. and then transferred to storage in liquid nitrogen. Thirty-five ampules containing approximately 200–300 epithelial organoids obtained in this example from specimen number 184 were stored frozen in liquid nitrogen.

Cell Culture. Primary cultures were initiated from the cryopreserved organoids by quick thawing and seeding the contents of one ampule into seven to nine T-25 flasks containing 2 ml of medium. The organoids were carefully dripped onto the surface of the flask with a 1-ml pipette. Then 2 ml of medium was added. After twenty-four hours, most organoids appeared firmly attached to the flask, and an additional 2 ml of medium was added. Cultures were routinely fed three times a week.

Cell migration from the organoids was visible twenty-four to forty-eight hours after seeding. In MM, mitotic activity was visible after forty-eight hours, and there was subsequent rapid growth to near confluence within 5–8 days after seeding. The deposited cell lines of the present invention were derived from cells grown in the MM medium. Cell growth in MCDB170 was slower, 10–14 days being required to achieve confluence (cells grown in this latter medium were not used to provide the deposited cells lines of the subject invention, although equivalent cells lines may emerge using MCDB170).

Subconfluent primary cultures of human mammary epithelial cells were then exposed to benzo[a]pyrene as follows. Five milliliters of medium containing 1μg of benzo[a]pyrene per ml dissolved in 2.5 μl of dimethyl sulfoxide was placed on the cells for twenty-four hour periods. Control cells received the dimethylsulfoxide alone. The treated cells showed 80% inhibition of colony formation when plated as single cells in secondary culture immediately after the twenty-four hour benzo[a]pyrene exposure.

Growth Response After Benzo[a]pyrene Exposure. Three separate experiments were conducted in which a frozen ampule of epithelial organoids from an HMEC specimen was seeded in primary culture in medium MM and two T-25 flasks containing actively dividing cultures were exposed to 1.0 μg of benzo[a]pyrene per ml for two or three twenty-four hour periods. Two of these experiments gave rise to the cell lines of the present invention. The exact time after initial seeding for exposure to benzo[a]pyrene and subculture varied among the three experiments. Treated and control primary cultures were repeatedly subjected to partial trypsinization (PT), wherein about half of the cells were removed and the remaining cells were allowed to regrow. After some PT, the removed cells were seeded into secondary cultures. The number of cells seeded per passage varied slightly, but a minimum of $4 \times 10^5$ cells (seeded at $5 \times 10^3$ cells per cm$^2$) was plated each time.

An extended growth potential was consistently observed in all of the treated cultures. Control cultures in medium MM normally maintained cell division for four or five passages when seeded after 1–5 PT and for fewer subcultures with increasing numbers of PT. After 8–12 PT, no growth occurred upon subculture. In contrast, the benzo[a]pyrene-treated cells seeded after 1–5 PT displayed some active growth for 5–10 passages. Foci of active growth also persisted in the primary cultures, even after 15 PT, and cultures seeded from these foci generally grew for another 7–10 passages in medium MM. Cells which continued to grow after treatment with benzo[a]pyrene when untreated cells would have ceased growth were designated "extended life" (EL) cultures.

Emergence of Continuous Cell Lines. Two continuous cell lines were then developed from these latter "extended life" cultures as follows. In experiment A, at the 9th PT, benzo[a]pyrene-treated and control cells were seeded into secondary culture. Both cultures grew rapidly to passage 4, when widespread presence of squamous, senescent cells was observed. In the treated cultures, focal areas of mitotic cells were still present at passage 5. One such cell patch was designated cell strain 184Aa. Upon subculture, these cells maintained active growth in medium MM up to passage 9, when the cell population from one subculture was observed to contain both the original patchy-growth type as well as smaller cells that grew as singlets with minimal cell-cell contact at low densities. None of the patchy cell type progeny of the 184Aa strain from any subculture lineage maintained active growth past passage 10 in medium MM, but the "singlet" cell type had continued growth. This first continuous line, designated 184A1, has been carried up to passage 74 with about a 20-fold cell increase per passage and a 24- to 36-hour doubling time in medium MM. Light microscope examination of early passage cell populations showed a very heterogeneous cell morphology, with both the small cell type and very large, vacuolated cells present. By passage 25, only rare large cells were observed, and higher passage populations consisted mainly of the small cell type, although they still appeared more heterogeneous than the untreated cell populations and grew with less cell-cell contact at low densities.

The second continuous cell line was developed in experiments B, in which secondary cultures were seeded at the 10th PT for the benzo[a]pyrene-treated cells and at the 13th PT for the controls. At that point, the treated cells showed foci of active growth, whereas the control cells had little mitotic activity. No control cells maintained growth at 2nd passage. Secondary cultures of the benzo[a]pyrene-treated cells showed foci of active growth, two actively growing patches with apparently normal light microscope morphology. These EL cells, designated 184Be, grew rapidly until 5th passage, when the growing cells became mixed with squamous senescent cells. By 6th passage, most cells were senescent, but focal areas of growing cells were still present. One small tightly packed patch of dividing cells was observed that appeared morphologically unique. These cells, designated 184B5, grew continuously upon subculture, maintaining growth as colonies of tightly packed cells.

Cellular Characterization. Several assays were performed to determine that the continuous lines 184A1 and 184B5 were indeed derived from the original human mammary epithelial cell specimen and that the cells were not in fact malignant. Immunofluorescent assays carried out with cells at various passage levels showed that virtually 100% of the cell population from both lines contained epithelial-specific keratin fibrils and thioesterase II, a mammary epithelial cell-specific enzyme. They also maintained the HMEC-specific pattern of powdery cell-associated fibronectin distribution. No grossly obvious differences between the cell lines and the untreated controls were evidenced. The human mammary milk fat globule antigens, another marker largely specific to HMEC, was also present in both cell lines. However, in this case, the cell lines differed from the untreated controls and resembled tumor-derived cells in their somewhat increased expression of these antigens.

To confirm that the cell lines were derived from the original specimen, 184A1 cells (43rd passage), 184B5 cells (18th passage), and untreated cells (7th passage) were analyzed for their profile of seven different polymorphic isozymmes by the method described in Halton, et al., "Cell Culture Quality Control by Rapid Isoenzymatic Characterization," (In Vitro 19 (1): 16-24 (1983), the disclosure of which is hereby incorporated by reference. All three cell types had an identical profile (the probability that such a result would occur by chance is less than 0.01%).

To determine if the cell lines displayed properties associated with malignant transformation, tumorigenicity in athymic nude mice was assayed using 5-10 mice per assay. Adult and newborn mice were injected subcutaneously with $1-2 \times 10^7$ normal, untreated, thirdpassage cells used as a control, 184A1 (34th passage), and 184B5 (21st passage). No tumors were observed.

Cells grown in medium MM were also tested for anchorage-independent growth (AIG) by suspending 105 single cells in 5 ml of a 1.25% methocel solution made up in medium MM and seeding into 60-mm Petri dishes. Plates were fed once a week and colonies (greater than 50 μm in diameter) were counted and sized after three weeks by using a calibrated ocular grid. Breast tumor cell line Hs578T (see Hackett, et al., supra) was used as a positive control. Control cells and 184A1 (tested at passage 11-36) showed no colony formation. Cell line 184B5 (tested at passages 26 and 27) showed 0.014% and 0.001% frequency of colony formation (less then 150 μm in diameter).

Metabolic Assays. Glucose metabolites were assayed in subconfluent monolayers in 35-mm culture dishes. Cells were exposed to fresh medium containing 50-100 μCi (1 Ci - 37 GBq) of $^{14}$C-labelled glucose (Amersham Corp., Arlington Heights, IL) for one and two hour periods and the cell lysate and medium were analyzed by two-dimensional paper chromatography. A portion of each cell sample was applied to Whatman No. 1 paper (22 × 18 in.) to separate the glucose metabolites. A portion of medium was applied to a second paper to analyse the metabolites secreted by the cells. The papers were run in phenol:water:acetic acid (84:16:1) for twenty-four hours. After drying, they were turned 90° and run in butanol:water:propionic acid (50:28:22) for another twenty-four hours. Benzo[a]pyrene metabolites from the medium and cells were assayed in subconfluent cultures exposed to 0.1 μg of tritiated benzo[a]pyrene per ml (19-40 Ci/mmol, Amersham) for sixteen hours, by eluting the spots and rechromatographing the samples with pure standards.

The original cell strains and continuous lines were thus examined as outlined above, by two different assays, to monitor effects of medium, state of functional differentiation, and/or continued passage in culture. It was observed that production of the glucose metabolites glycogen and lactate varied considerably with the growth medium employed. Table 1 indicates that glycogen production was decreased in 184Aa cells grown in medium MM, wheras lactate production was similar to the normal cells and responsive to media modulation. Early-passage 184Al cells also made little glycogen and, additionally, displayed decreased lactate synthesis and extremely high fructose diphosphate formation. By later passages, these additional alterations had disappeared and the cell line behaved similar to the 184Aa strain. The 184B5 cell line at early passage behaved more like normal cells in the amount and modulation of lactate production, but glycogen synthesis was decreased. Table 1 illustrates the glucose metabolite pattern of normal versus benzo[a]pyrene-treated cells. The benzo[a]pyrene-treated cell strains and lines displayed decreases in benzo[a]pyrene metabolites similar to those previously found in untreated cells at equivalent passage levels, and increasing passage led to further large decreases. Table 2 illustrates the contrast between benzo[a]pyrene metabolism in normal versus benzo[a]pyrene-treated human mammary epithelial cells.

Karyology. With regard to morphology and enumeration of chromosomes, metaphases were stained with Giemsa following hypotonic treatment and air-drying. The trypsin-Giemsa method was used for a study of marker chromosomes and Q-banding. The two continuous cell lines obtained as outlined above display substantial genetic stability, as they maintained a near diploid karyotype upon continued passage in culture with substantially stable stem-line chromosome markers. Although cell line 184B5 shows some change upon passage, cell line 184A1 is extremely stable in this regard.

Specifically, the 184A1 line has been examined at passages 11, 23 and 32 (25 cells at each passage) an shows the same three stem line chromosome markers at all passages (3q−, monosomic 6, 12q−). Passages 23 and 32 also displayed more than two #20 chromosomes. Other chromosomal abnormalities are not present in the majority of the cell population. Cell line 184B5 has been examined at passage 11 and 41 (representing an increase of approximately 140 population doublings). While not every cell showed the identical karyotype at passage 11, the majority displayed the same stem cell chromosome markers (t(1q; 4q), t(1q; 8q), 10p−, 11q−, 15p+, 17p−, extra #20). At the 41st passage, these markers were still present. However, a few new markers were also found in some of the cells (i.e., unstable 1, unstable 2, t(2p; 5q), t(5p; 19p), i(5p), 11q+). Thus, some chromosomal changes can be seen upon long term passage of 184B5, but these are small for the number of intervening population doublings compared to existing human epithelial cell lines obtained from tumor specimens or transformation with tumor viruses.

Development of Malignant Cell Lines: It was then demonstrated that the cell lines could be neoplastically transformed as follows. 184B5 cells at 21st passage were exposed to a Kirsten mouse sarcoma virus (K-MSV) pseudotype of the endogenous baboon virus (K-MSV[BaEv]) which is infectious for human, but not mouse, cells. Clearly defined foci were visible, consisting of cells with an altered, swirly morphology with large piles of released cells floating above. The number of focus forming units was approximately equal to that seen when the same virus preparation was titered on normal rat kidney (NRK) cells. Cells infected at high titer were grown up and two passages later innoculated ($10^7$ cells) into adult nude mice. Nine out of nine mice developed large, cystic palpable tumors within 2-3 weeks. The removed tumors were classified as poorly differentiated carcinomas. The removed tumor cells have been reestablished in culture using either MCDB170, or MM without fresh serum. The cells appear larger and not as tightly packed as the parent 184B5 line.

TABLE 1

| | Glucose metabolites (nmol/mg of protein) of normal and benzo[a]pyrene HMEC | | | | | | | | | | | |
|---|---|---|---|---|---|---|---|---|---|---|---|---|
| | Untreated Cells | | 184 Aa | | 184 Al | | | | | | 184 B5 | |
| | | | | | MM | | | | MCDB170 | | | MCBD |
| | MM, passage 8* | MCDB170, passage 8 | MM, passage 8 | MCDB170, passage 8 | Passage 13 | Passage 17 | Passage 27 | Passage 42 | Passage 13 | Passage 42 | MM, passage 10 | 170, passage 11 |
| Metabolite | | | | | | | | | | | | |
| Glucose 6-phosphate | NT | 5.3 | 2.6 | 3.7 | 2.8 | 3.4 | 2.3 | 1.8 | 2.2 | NT | 2.6 | 2.4 |
| Fructose bisphosphate | NT | 3.2 | 2.0 | 1.0 | 28.0 | 37.6 | 2.0 | 1.0 | 47.9 | NT | 0.8 | 0.2 |
| 6-Phosphogluconate | NT | 1.2 | 0.8 | 0.5 | 6.1 | 5.1 | 2.1 | 1.4 | 3.4 | NT | 1.1 | 0.2 |
| Glycerol phosphate | NT | 5.6 | 2.4 | 1.7 | 1.5 | 2.2 | 3.6 | 4.2 | 1.6 | NT | 2.6 | 0.9 |
| Product | | | | | | | | | | | | |
| Glycogen | 142 | 12 | 6 | 5 | 2 | 8 | 10 | 8 | 2 | 4 | 20 | 1 |
| Lactate | 995 | 358 | 855 | 374 | 126 | 420 | 472 | 917 | 157 | 150 | 1184 | 85 |

Cells were grown in the indicated medium (MM or MCDB170) and analyzed for glucose metabolites. Each value for the metabolites is the mean of the 1- and 2-hour values. The values for glycogen and lactate are the means of the incorporations per hour at 1 and 2 hours. NT, not tested.
*Cells grown in the medium MCDB170 were transferred at 8th passage to medium MM for 72 hour prior to addition of glucose.

TABLE 2

| | Benzo[a]pyrene Metabolism in normal and benzo[a]pyrene-treated HMEC | | | | | | |
|---|---|---|---|---|---|---|---|
| | Specimen | | | | | | |
| | Untreated, passage 3 | 184Aa, passage 8 | 184 Al | | | 184 B5 | |
| | | | Passage 12 | Passage 26 | Passage 42 | Passage 11 | Passage 29 |
| Total benzo[a]pyrene conversion | 376 | 286 | 236 | 57 | 24 | 263 | 62 |
| Metabolites in medium | 323 | 243 | 203 | 41 | 15 | 215 | 56 |
| Water soluble | 194 | 105 | 56 | 7 | 6 | 103 | 20 |
| Sulfates | 19 | 19 | 7 | 1 | 1 | 19 | 3 |
| Glucuronides | 46 | 29 | 23 | 1 | 1 | 43 | 8 |
| Glutathiones | 129 | 157 | 26 | 5 | 5 | 41 | 9 |
| Organosoluble | 129 | 138 | 147 | 34 | 9 | 112 | 36 |
| Tetrols + 9,10-diol | 88 | 122 | 119 | 24 | 5 | 88 | 18 |
| 7,8-Dihydrodiol | 19 | 6 | 17 | 7 | 1 | 12 | 1 |
| Phenols | 15 | 8 | 6 | 3 | 3 | 12 | 10 |
| Other | 7 | 2 | 5 | 0 | 1 | 0 | 7 |
| Metabolites in cell | 53 | 43 | 33 | 16 | 9 | 48 | 6 |
| Water soluble | 10 | 12 | 9 | 5 | 4 | 11 | 1 |
| Organosoluble | 43 | 31 | 24 | 11 | 5 | 37 | 6 |

Cells were grown in medium MM and analyzed for benzo[a]pyrene metabolites. The metabolite results (nmol) are from subconfluent cultures grown in 60-mm dishes (5 ml) or T-75 flasks (15 ml).

It is to be understood that while the novel cell lines and processes of making and using the same having been described in conjunction with the preferred specific embodiments thereof, the description is intended to illustrate and not limit the scope of the invention, which is defined by the scope of the appended claims.

I claim:

1. A biologically pure cell culture comprising a continuous human cell line derived from normal human mammary epithelial cells by means of treatment with a chemical carcinogen and selected from the group consisting of the cell lines having ATCC deposit numbers CRL8798 and CRL 8799.

2. The composition of claim 1, wherein said cell line is a clone or subclone of ATCC deposit number CRL8798 or CRL8799.

3. The composition of claim 1, wherein said chemical carcinogen comprises a polycyclic aromatic hydrocarbon.

4. The composition of claim 3, wherein said polycyclic aromatic hydrocarbon is benzo[a]pyrene.

* * * * *